United States Patent [19]

Grozinger et al.

[11] Patent Number: 5,200,522
[45] Date of Patent: Apr. 6, 1993

[54] METHOD FOR PREPARING 3-AMINO-2-CHLORO-4-ALKYLPYRIDINES

[75] Inventors: Karl G. Grozinger, Ridgefield; Karl D. Hargrave, Brookfield; Julian Adams, Ridgefield, all of Conn.

[73] Assignee: Boehringer Ingelheim Pharmaceuticals, Inc., Ridgefield, Conn.

[21] Appl. No.: 714,129

[22] Filed: Jun. 11, 1991

[51] Int. Cl.$^5$ .......................................... C07D 213/73
[52] U.S. Cl. .................................... 546/250; 546/311
[58] Field of Search ................................ 546/250, 311

[56] References Cited

U.S. PATENT DOCUMENTS 3,655,679  4/1972  Shen et al. ........................... 546/311
4,001,252  1/1977  Meyer et al. ......................... 546/311

OTHER PUBLICATIONS

Lounasmaa, et al., "Tetrahedron", vol. 33, 1977, pp. 113-117.
Bobbitt, et al., J. Org. Chem. vol. 25, 1960, pp. 560-564.
Morisawa, et al., "J. Med. Chem.", vol. 21, No. 2, 1978, pp. 194-199.
Schickh, et al., "Berichte der Deutschen Chemischen", Nr. 12, 1936, p. 2605.
Schmitz, et al., "Archiv. d. Pharmazic", vol. 308, 1975, pp. 433-437.

Primary Examiner—C. Warren Ivy
Assistant Examiner—James H. Turnipseed
Attorney, Agent, or Firm—David E. Frankhouser; Daniel Reitenbach; Mary-Ellen M. Timbers

[57] ABSTRACT

A process for the preparation of a 3-amino-2-chloro-4-alkylpyridine of the formula:

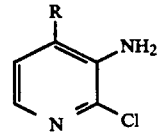

wherein R is alkyl of from one to three carbon atoms, an intermediate in the preparation of certain 5,11-dihydro-6H-dipyrido[3,2-b:2',3'-e][1,4]diazepine compounds useful in the prevention and treatment of HIV infection.

7 Claims, No Drawings

METHOD FOR PREPARING 3-AMINO-2-CHLORO-4-ALKYLPYRIDINES

FIELD OF THE INVENTION

This invention relates to a novel method for preparing certain 3-amino-2-chloro-4-alkylpyridines.

BACKGROUND OF THE INVENTION

Copending U.S. Patent application Ser. No. 600,390, filed Oct. 19, 1990, entitled "5,11-Dihydro-6H-Dipyrido[3,2-b:2',3'-e[1,4]Diazepines and Their Use in the Prevention or Treatment of HIV Infection", describes novel 5,11-dihydro-6H-dipyrido[3,2-b:2',3'-e][1,4]diazepines useful in the prevention and treatment of HIV infection and methods for preparing these compounds.

3-Amino-2-chloro-4-alkylpyridines are useful intermediates in the preparation of 4-alkyl-5,11-dihydro-6H-dipyrido[3,2-b:2',3'-e]-[1,4]diazepines.

SUMMARY OF THE INVENTION

3-Amino-2-chloro-4-alkylpyridines prepared by the novel process of this invention have the formula:

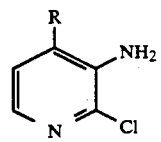
(I)

wherein R is alkyl of from one to three carbon atoms.

The process for this invention for the preparation of the compound of formula I is outlined below:

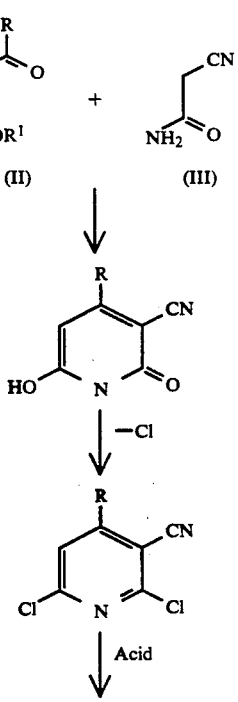

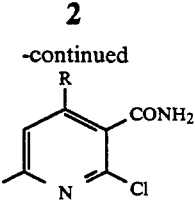
(VI)

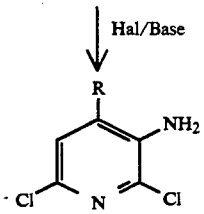
(VII)

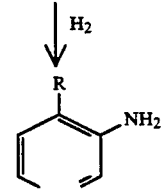
(VIII)

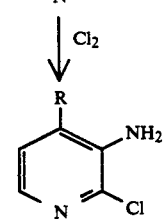
(I)

DETAILED DESCRIPTION OF THE INVENTION

The novel process of this invention for preparing the 3-amino-2-chloro-4-alkylpyridine of formula I comprises the following steps:

Step 1, reacting a compound having the formula:

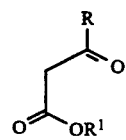
(II)

wherein R and $R^1$ are each alkyl of from one to three carbon atoms, with cyanoacetamide

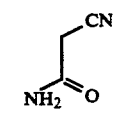
(III)

in the presence of an organic solvent such as methanol or ethanol, with a base, such as KOH, at a temperature ranging from 50° C. to 80° C., for 4 to 8 hours, to produce a compound of the formula:

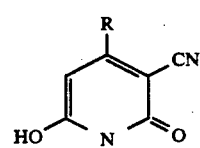
(IV)

Step 2, reacting the compound produced in Step 1 with a chlorinating agent, such as phenylphosphonic dichloride or inorganic acid halides such as phosphorous oxychloride, at a temperature of 110° C. to 180° C., for 6 to 24 hours, to produce a compound of the formula:

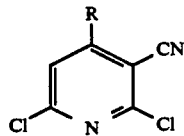

(V)

Step 3, heating the compound produced in Step 2 in the presence of an acid such as concentrated sulfuric acid, at a temperature of 80° C. to 110° C., for 1 to 10 hours, to produce a compound of the formula:

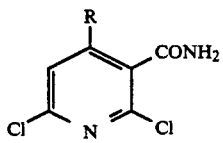

(VI)

Step 4, reacting the compound produced in Step 3 with a base such as NaOH, and a halide such chlorine or bromine, at a temperature of 0° C. to 100° C., for 1 to 10 hours, to produce a compound of the formula:

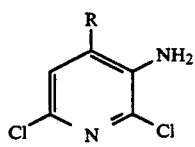

(VII)

Step 5, hydrogenating the compound produced in Step 4 in the presence of an organic solvent such as methanol, ethanol or tetrahydrofuran (THF), with a hydrogenation catalyst such palladium chloride or a palladium metal, in the presence of a base such as sodium acetate, at 50 to 150 psi, at a temperature of 20° C. to 100° C., for 6 to 24 hours, to produce a compound of the formula:

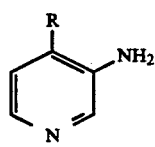

(VIII)

Step 6, contacting the compound produced in Step 5 with chlorine gas at a pH of 0.01 to 2, at a temperature of 5° C. to 30° C., for 0.5 to 2 hours, to produce the compound of formula I.

Example I illustrates the preparation of the 3-amino-2-chloro-4-alkylpyridines of formula I.

EXAMPLE I

Preparation of 3-amino-2-chloro-4-methylpyridine

A) Preparation of 3-cyano-2,6-dihydro-4-methylpyridine

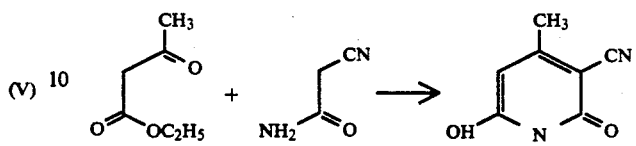

A mixture of 336g (4 moles) of cyanoacetamide, 507ml (520g, 4 moles) of ethyl acetoacetate, and 850ml of methanol was warmed to attain solution then 275g (4.18 moles) of potassium hydroxide dissolved in 200ml of methanol was added during 2 hours with stirring. During the addition a white precipitate formed and more methanol was added to prevent caking. The mixture was heated to reflux, stirred for 8 hours, cooled and filtered. The white precipitate was washed with methanol. The mono potassium salt was dissolved in warm water, filtered, cooled, acidified with concentrated hydrochloric acid, filtered, washed with water, and dried at 90° C. to yield 535g (89%).

B) Preparation of 3-cyano-2,6-dichloro-4-methylpyridine

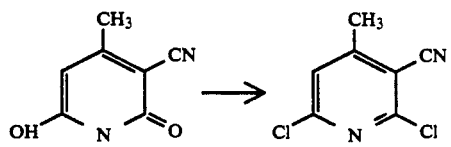

Method 1

3-Cyano-2,6-dihydroxy-4-methylpyridine (30g, 0.2 mole) and phosphorous oxychloride (80ml) were placed in a glass lined stainless steel autoclave and heated to 110–140° C. for 18 hours. (A pressure of 110–130 psi was obtained.) After cooling, the mixture was poured into 300ml of warm water (30–40° C.). During the hydrolysis, the mixture was maintained at 30–40° C. by the intermittent addition of ice. The crystalline product was filtered and washed with water and dried. The material was crystallized from hot ethanol to yield 33.7g (mp 102–106° C.) (90%).

Method 2

A 5 liter 3-neck round bottom flash equipped with overhead stirrer, thermometer, and reflux condenser was charged with 810 ml (5.7 mole) phenylphosphonic dichloride. The solution was heated with stirring to an internal temperature of 100° C., then 288g (1.9 mole) of 2,6-dihydroxy-3-cyano-4-methylpyridine was added in portions over 45 minutes, keeping the internal temperature at 100–105° C. The mixture was then heated to 140–145° C. for 2 hours. After cooling the solution to 70° C., 2 liters of toluene was added with stirring. The mixture was poured cautiously over 2 liters of H$_2$O, and stirred for one hour at room temperature. The organic layers were separated. The aqueous phase was back-extracted with 2 liter of toluene. During the extraction, C$_6$H$_5$PO$_2$ separated, which was filtered off. The solid was washed with toluene and finally discarded. The combined organic layers were dried over anhydrous Na$_2$SO$_4$, filtered, and the solvent evaporated. The solid was stirred with ethanol, and air dried to give a light yellow solid, wt: 272.5 g (76.7%); mp 100–105° C.

C) Preparation of 2,6-dichloro-4-methyl-3-pyridinecarboxamide

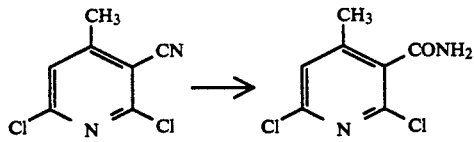

A mixture of 3-cyano-2,6-dichloro-4-methylpyridine (270g, 1.44 mole) and concentrated sulfuric acid (530ml) was heated and stirred at 100–110° C. for 3 hours. The resultant mixture was cooled, and poured, with stirring, into 2l of water, to produce a precipitate. The precipitate was neutralized with a sodium hydroxide solution and stirred overnight. The precipitate was then filtered, washed with 3l of water, and dried at 80° C. under vacuum.

Yield: 277g (93.8%) mp 169–173° C.

D) Preparation of 2,6-dichloro-4-methyl-3-aminopyridine

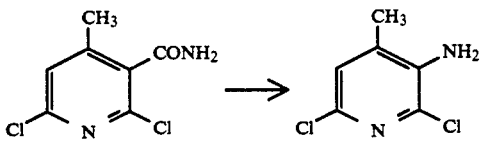

A solution of 204.4g (5.11 mole) of sodium hydroxide in 1950ml of water was stirred and cooled to 0–5° C. 78.8ml (1.53 mole) of bromine was then added dropwise to the solution over 30 minutes, maintaining the temperature of the resultant solution at 0–5° C., to produce a sodium hypobromite solution. To the sodium hypobromite solution, Was added 275g (1.34 mole) of 2,6-dichloro-4-methyl-3-pyridinecarboxamide over 10 minutes, maintaining the temperature of resultant mixture at 0–5° C. The resultant mixture was slowly brought to room temperature over one hour and then heated at 70–75° C. for one hour, to produce a suspension. The suspension was cooled to room temperature, and stirred overnight. The resultant precipitate was filtered, washed with 2l of water and dried at 60° C., to give 217.9g (91.8%) of 2,6-dichloro-4-methyl-3-aminopyridine (mp 83–85° C.).

E) Preparation of 3-amino-4-methylpyridine

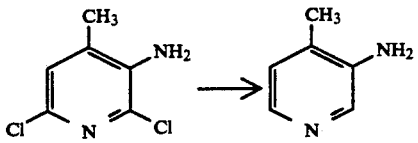

Method 1

A mixture of 108g (0.61 mole) of 3-amino-2,6-dichloro-4-methylpyridine, 100g of anhydrous sodium acetate and 1.55–2.5g of PdCl$_2$ in 550ml of methanol was hydrogenated at 60–80° C., using a 2l stirred stainless steel "PARR" hydrogenator at 50 psi for 24 hours. The PdCl$_2$ was filtered off and washed with methanol, to produce a filtered mixture minus PdCl$_2$. The filtered mixture was concentrated, then diluted with 300ml of water and basified with 6N potassium hydroxide solution. The resultant product was extracted with 4×400ml of methylene chloride and dried over anhydrous Na$_2$SO$_4$, to produce an organic phase and an aqueous phase. The organic phase was concentrated and then 350ml of ether was added with stirring to give a crystalline solid. After filtration, 57.7g (87.5%) of 3-amino-4-methylpyridine was obtained (mp 100–104° C.).

Method 2

The same procedure as described in Method 1 was used except that 10g of 10% Pd/C was used instead of the PdCl$_2$. 60g (91%) of 3-amino-4-methylpyridine was obtained (mp 101–104° C.).

F) Preparation of 3-amino-2-chloro-4-methylpyridine

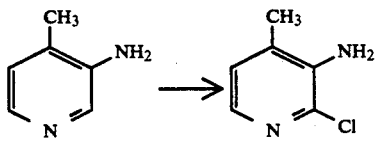

3-Amino-4-methylpyridine (21.6g, 0.2 mole) was suspended in 75 ml of water at room temperature. The mixture was dissolved by the addition of 25 ml conc. hydrochloric acid. The solution was cooled to 20° C. and 15.6 g (0.22 mole) of chlorine gas was introduced through an inlet tube reaching below the surface of the reaction mixture over 25 minutes. The mixture was stirred under a nitrogen purge for an additional 30 minutes, then cooled to 10° C. and basified by the addition of 70 mL of a 12.5 N. sodium hydroxide solution. Additional water (100 mL) was added to maintain efficient agitation of the mixture. The precipitate was collected, washed with water and dried to give 14.5g of the title product. The aqueous phase was extracted with 3 times 100 mL of methylene chloride. The organic phases were washed with water, dried over magnesium sulfate, and concentrated to give an additional 9.4g, mp 62–64° C. Total yield, 23.9g (84%).

What is claimed is:

1. A process for the preparation of a 3-amino-2-chloro-4-alkylpyridine of the formula:

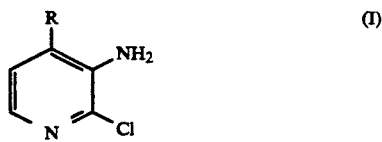

wherein R is alkyl of from one to three carbon atoms, which comprises the steps of:

a) reacting a compound of the formula:

wherein R is as defined above and R$^1$ is alkyl from one to three carbon atoms, with cyanoacetamide and a hydroxide of an alkali metal, in the presence of an organic solvent, at a temperature of from 60° C. to 80° C., for 1 to 4 hours, to produce a compound of the formula:

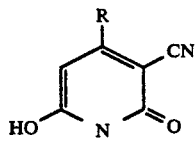

(IV)

b) reacting the compound produced in a) with phosphorous oxychloride or phenylphosphonic dichloride, at a temperature of 110° C. to 180° C., for 6 to 24 hours, to produce a compound of the formula:

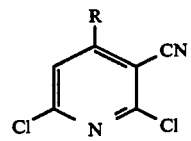

(V)

c) heating the compound produced in b) in the presence of an inorganic acid, at a temperature of from 80° C. to 110° C., for 1 to 10 hours, to produce a compound of the formula:

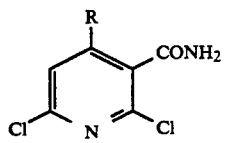

(VI)

d) reacting the compound produced in c) with a hydroxide of an alkali metal and a halide at a temperature of 0° C. to 100° C., for 1 to 10 hours, to produce a compound of the formula:

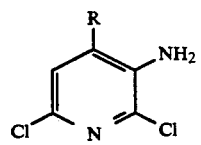

(VII)

e) hydrogenating the compound produced in d) in the presence of hydrogen and an organic solvent and a base, with palladium dichloride or palladium metal, at 50 to 150 psi, at a temperature of from 20° C. to 100° C., for 6 to 24 hours, to produce a compound of the formula:

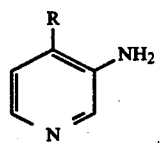

(VIII)

f) contacting the compound produced in e) with hydrochloric acid and chlorine gas, at a pH of 0.01 to 2, at a temperature of 5° C. to 30° C. for 0.5 to 2 hours, to produce the 3-amino-2-chloro-4-alkylpyridine of formula I.

2. A process as recited in claim 1 wherein:
i) the organic solvent in a) is methanol or ethanol and the hydroxide of an alkali metal in a) is KOH;
ii) the inorganic acid in c) is concentrated sulfuric acid;
iii) the hydroxide of an alkali metal in d) is NaOH and the halide is bromine and chlorine; and
iv) the organic solvent in e) is methanol, ethanol or THF.

3. A process as recited in claim 2 wherein in b), the compound produced in a) is reacted with phosphorous oxychloride and then any excess phosphorous oxychloride is hydrolyzed at a temperature of from 30° C. to 50° C. for 0.5 to 1 hour.

4. A process as recited in claim 1 wherein R is methyl.

5. A process for the preparation of 3-amino-2-chloro-4-methylpyridine, which comprises the steps of:
a) reacting ethyl acetoacetate with cyanoacetamide and a hydroxide of an alkali metal, in the presence of an organic solvent, at a temperature of from 60° C. to 80° C., for 1 to 4 hours, to produce 3-cyano-2,6-dihydro-4-methylpyridine;
b) reacting 3-cyano-2,6-dihydro-4-methylpyridine produced in a), with phosphorous oxychloride or phenylphosphonic dichloride, at a temperature of 110° C. to 180° C., for 6 hours to 24 hours, to produce 3-cyano-2,6-dihydro-4-methylpyridine;
c) heating the 3-cyano-2,6-dihydro-4-methylpyridine produced in b), in the presence of an inorganic acid, at a temperature of from 80° C. to 110° C., for 1 hours to 10 hours, to produce 2,6-dihydro-4-methyl-3-pyridinecarboxamide;
d) reacting the 2,6-dihydro-4-methyl-3-pyridinecarboxamide produced in c), with a hydroxide of an alkali metal and a halide, at a temperature of 0° C. to 100° C., for 1 hours to 10 hours, to produce 2,6-dihydro-4-methyl-3-aminopyridine;
e) hydrogenating the 2,6-dihydro-4-methyl-3-aminopyridine produced in d), in the presence of hydrogen and an organic solvent, with palladium dichloride or palladium metal, at 50 to 150 psi, at a temperature of from 20° C. to 100° C., for 6 to 24 hours, to produce 3-amino-4-methylpyridine; and
f) contacting the 3-amino-4-methylpyridine produced in e), with hydrochloric acid and chlorine gas at a pH of 0.01 to 1, at a temperature of from 5° C. to 30° C., for 0.5 to 2 hours, to produce 3-amino-2-chloro-4-methylpyridine.

6. A process as recited in claim 5 wherein:
i) the organic solvent in a) is methanol or ethanol and the hydroxide of an alkali metal in a) is KOH;
ii) the inorganic acid in c) is concentrated sulfuric acid;
iii) the hydroxide of an alkali metal in d) is NaOH and the halide is bromine and chlorine; and
iv) the organic solvent in e) is methanol, ethanol or THF.

7. A process as recited in claim 6 wherein in b), the compound produced in a) is reacted with phosphorous oxychloride and then any excess phosphorous oxychloride is hydrolyzed at a temperature of from 30° C. to 50° C. for 0.5 to 1 hour.

* * * * *